United States Patent
Rao et al.

[11] Patent Number: 5,880,315
[45] Date of Patent: *Mar. 9, 1999

[54] CATALYTIC MANUFACTURE OF VINYL FLUORIDE

[75] Inventors: V.N. Mallikarjuna Rao, Wilmington, Del.; Munirpallam A. Subramanian, Kennett Square, Pa.

[73] Assignee: E. I. du Pont de Nemours and Company, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 964,445

[22] Filed: Nov. 4, 1997

Related U.S. Application Data

[60] Provisional application No. 60/031,589 Nov. 21, 1996.

[51] Int. Cl.⁶ .................................................... C01C 17/25
[52] U.S. Cl. ............................................ 570/157; 570/158
[58] Field of Search ...................................... 570/157, 158

[56] References Cited

U.S. PATENT DOCUMENTS

| | | |
|---|---|---|
| 2,599,631 | 6/1952 | Harmon . |
| 3,505,416 | 4/1970 | Davis et al. ............................. 570/158 |
| 3,505,418 | 4/1970 | Davis et al. ............................. 570/158 |
| 5,559,069 | 9/1996 | Rao et al. ............................... 502/226 |

*Primary Examiner*—Alan Siegel

[57] ABSTRACT

A process for the manufacture of vinyl fluoride (i.e., $CH_2=CHF$, VF or 1141) from 1,1-difluoroethane (i.e., $CH_3CHF_2$, F152a or HFC-152a) is disclosed which involves contacting the 1,1-difluoroethane at an elevated temperature (200° C.–400° C.) with a multiphase catalyst composition consisting essentially of (a) fluorides of at least one divalent metal selected from magnesium and zinc, and (b) fluorides of trivalent aluminum, in which phases of the divalent fluorides are homogeneously dispersed with phases of the trivalent fluorides.

8 Claims, No Drawings

CATALYTIC MANUFACTURE OF VINYL FLUORIDE

This application claims the priority benefit of U.S. Provisional Application 60/031,589, filed Nov. 21, 1996.

FIELD OF THE INVENTION

This invention relates to processes for the production of vinyl fluoride, and more particularly, to catalysts and to a catalytic process for the dehydrofluorination of 1,1-difluoroethane to vinyl fluoride.

BACKGROUND

Vinyl fluoride is a useful monomer for the preparation of fluorocarbon polymers which have excellent weathering and chemical resistance properties.

Vinyl fluoride can be produced from acetylene and hydrogen fluoride using mercury catalysts. It can also be produced by the dehydrofluorination of 1,1-difluoroethane. The dehydrofluorination of 1,1-difluoroethane to vinyl fluoride and hydrogen fluoride is an equilibrium reaction. According to published literature the following equilibrium concentrations of vinyl fluoride (VF), based on the moles of VF divided by the moles of HFC-152a+VF, have been determined; about 13% VF at 227° C., about 40% VF at 327° C. and about 99% VF at 427° C.

U.S. Pat. No. 2,599,631 discloses a process for the manufacture of vinyl fluoride by the dehydrofluorination of HFC-152a. The dehydrofluorination is done in the presence or absence of a catalyst. The dehydrofluorination catalysts disclosed include oxygen, charcoal, and the free metals, salts and oxides of the elements of Groups IA, IB, IIA, IIB, VB and VIII of the periodic table. In an example using the divalent Group II metal compound calcium fluoride as a catalyst (at about 500° C.), the conversion of HFC-152a to vinyl fluoride was 66% (i.e., about 66% of equilibrium). There is an ongoing interest in developing more efficient catalysts for the conversion of HFC-152a to VF.

SUMMARY OF THE INVENTION

A process is provided for the manufacture of vinyl fluoride (i.e., $CH_2=CHF$, VF or 1141) from 1,1-difluoroethane (i.e., $CH_3CHF_2$, F152a or HFC-152a) which comprises contacting said 1,1-difluoroethane at an elevated temperature with a catalyst containing at least one divalent Group II metal compound. The process of this invention is characterized by contacting said 1,1-difluoroethane at a temperature of from about 200° C. to 400° C. with a multiphase catalyst composition consisting essentially of (a) fluorides of at least one divalent metal selected from magnesium and zinc, and (b) fluorides of trivalent aluminum; wherein phases of said divalent fluorides are homogeneously dispersed with phases of said trivalent fluorides.

DETAILED DISCUSSION

The present invention provides a process for the manufacture of vinyl fluoride by contacting 1,1-difluoroethane in the vapor phase in the presence of homogeneously dispersed mutiphase catalyst compositions. Of note for use in this process are catalyst compositions selected from the group consisting of magnesium fluoride/aluminum fluoride compositions, zinc fluoride/aluminum fluoride compositions and zinc fluoride/magnesium fluoride/aluminum fluoride compositions where the atomic ratio of Mg:Al, Zn:Al, and (Zn+Mg):Al are all respectively about 1:1.

These catalyst compositions can be prepared as described in U.S. Pat. No. 5,559,069 which is hereby incorporated herein by reference (see in particular Examples 1 to 4). For example, these catalyst compositions can be prepared by heating a single phase fluoride composition of the formula $MAlF_5(H_2O)_2$ or the formula $NH_4MAlF_6(H_2O)$ where M is at least one divalent element selected from the group consisting of Zn and Mg, to a temperature sufficient to substantially remove $H_2O$ (and $NH_4F$ when $NH_4^+$ is present) in said single phase fluoride composition.

The physical shape of the catalyst is not critical and may, for example, include pellets, powders or granules.

The reaction temperature will normally be within the range from about 200° C. to about 400° C., preferably about 225° C. to 375° C. To provide for low acetylene formation and to enhance catalyst life, the temperature is preferably kept within the range of from about 250° C. to about 350° C., more preferably, from about 250° C. to about 325° C.

The 1,1-difluoroethane is typically passed over the catalyst at a rate of about 60 volumes to about 3600 volumes per volume of catalyst per hour; preferably 120 volumes to 720 volumes per volume of catalyst per hour. These volumes correspond to a contact time of about 60 seconds to about 1 second and preferably about 30 seconds to about 5 seconds. Normally a contact time is employed which is sufficient to provide a dehydrofluorination of HFC-152a equal to at least 50% of the equilibrium value for conversion of 1,1-difluoroethane to vinyl fluoride at the temperature employed; preferably at least 80%, and more preferably at least 90% of the equilibrium value at a given reaction temperature.

The reaction pressure can be subatmospheric, atmospheric or superatmospheric. Generally, near atmospheric pressures are preferred.

Unreacted starting material can be recycled to the reactor for the production of additional $CH_2=CHF$. Vinyl fluoride (b.p. −72° C.) may be recovered from the reaction product and any unreacted 1,1-difluoroethane (b.p. −25° C.) by conventional procedures such as distillation.

The process of this invention can be carried out readily in the vapor phase using well known chemical engineering practice.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

Legend
 1141 is $CH_2=CHF$  F152a is $CH_3CHF_2$

PREPARATION OF CATALYSTS

Preparation of $MgF_2$/beta-$AlF_3$ and $ZnF_2$/beta-$AlF_3$:

$MgF_2$/beta-$AlF_3$ and $ZnF_2$/beta-$AlF_3$ corresponding to the atomic ratio 1:1:5 for Mg:Al:F and Zn:Al:F, respectively, were prepared according to procedures described in U.S. Pat. No. 5,559,069.

EXAMPLE 1

$ZnF_2$/beta-$AlF_3$ (5.1 gm, 5 mL) was placed in a ½" (1.3 cm)×11" (27.9 cm) Hastelloy™ nickel alloy tubular reactor.

The catalyst was dried by heating to 350° C. for 16 hours under a flow of dry nitrogen of 50 sccm (8.3×10⁻⁷ m³/s) prior to use. The reactor was cooled to 275° C. and a flow of F152a was begun at 50 sccm (8.3×10⁻⁷ m³/s). The contact time was 6 seconds. The results are shown in Table 1.

TABLE 1

| Total Hours | Temp (°C.) | % F152a | % 1141 |
|---|---|---|---|
| 1.0 | 275 | 65.7 | 34.3 |
| 720.4 | 275 | 64.7 | 35.3 |

EXAMPLE 2

MgF$_2$/beta-AlF$_3$ (1 mL, 12–20 mesh (1.68–0.84 mm)) was placed in a ¼" (0.64 cm)×3" (7.6 cm) tubular Hastelloy™ nickel alloy reactor. The reactor was heated to 300° C. and a flow of F152a was begun at 10 sccm (1.7×10⁻⁷ m³/s) to give a contact time of 6 sec. The results are shown in Table 2.

TABLE 2

| Total Hours | Temp (°C.) | % F152a | % 1141 |
|---|---|---|---|
| 1.0 | 300 | 57.2 | 42.8 |
| 24.0 | 300 | 57.2 | 42.8 |
| 48.0 | 300 | 56.6 | 43.4 |

EXAMPLE 3

The reactor was the same as that of Example 2. ZnF$_2$/beta-AlF$_3$ (1 mL, 12–20 mesh (1.68–0.84 mm)) was heated to 300° C. and a flow of HFC-152a was begun at 10 sccm (1.7×10⁻⁷ m³/s) to give a contact time of 6 sec. The results are shown in Table 3.

TABLE 3

| Total Hours | Temp (°C.) | % F152a | % 1141 |
|---|---|---|---|
| 1.0 | 300 | 55.2 | 44.8 |
| 24.0 | 300 | 55.7 | 44.3 |
| 48.0 | 300 | 56.5 | 43.5 |

We claim:

1. A process for the manufacture of vinyl fluoride from 1,1-difluoroethane which comprises contacting said 1,1-difluoroethane at an elevated temperature with a catalyst containing at least one divalent Group II metal compound, characterized by:

contacting said 1,1-difluoroethane at a temperature of from about 200° C. to 400° C. with a multiphase catalyst composition consisting essentially of (a) fluorides of at least one divalent metal selected from magnesium and zinc, and (b) fluorides of trivalent aluminum; wherein phases of said divalent fluorides are homogeneously dispersed with phases of said trivalent fluorides.

2. The process of claim 1 wherein the catalyst is prepared by heating a single phase fluoride composition of the formula MAlF$_5$(H$_2$O)$_2$ or the formula NH$_4$MAlF$_6$(H$_2$O) where M is at least one divalent element selected from the group consisting of Zn and Mg, to a temperature sufficient to substantially remove H$_2$O, and NH$_4$F when NH$_4^+$ is present, in said single phase fluoride composition.

3. The process of claim 1 wherein the catalyst is a magnesium fluoride/aluminum fluoride composition where the ratio of Mg:Al is about 1:1.

4. The process of claim 1 wherein the catalyst is a zinc fluoride/aluminum fluoride composition where the ratio of Zn:Al is about 1:1.

5. The process of claim 1 wherein the catalyst is a magnesium fluoride/zinc fluoride/aluminum fluoride composition where the ratio of (Zn+Mg):Al is about 1:1.

6. The process of claim 1 wherein the temperature is from 250° C. to 350° C.

7. The process of claim 1 wherein the temperature is from 250° C. to 325° C.

8. The process of claim 1 wherein a contact time is employed which is sufficient to provide a dehydrofluorination of 1,1-difluoroethane equal to at least 80% of the equilibrium value for conversion of 1,1-difluoroethane to vinyl fluoride at the temperature employed.

* * * * *